United States Patent [19]

Ono

[11] Patent Number: 5,469,488
[45] Date of Patent: Nov. 21, 1995

[54] X-RAY CT SCANNER

[75] Inventor: Masahiko Ono, Otawara, Japan

[73] Assignee: Kabushiki Kaisha Toshiba, Kanagawa, Japan

[21] Appl. No.: 305,842

[22] Filed: Sep. 14, 1994

[30] Foreign Application Priority Data

Sep. 16, 1993 [JP] Japan ................................. 5-230543

[51] Int. Cl.$^6$ ........................................ H05G 1/02
[52] U.S. Cl. ........................ 378/15; 378/19; 250/551
[58] Field of Search ............................. 378/15, 19, 4, 378/205, 206; 250/551; 359/368, 369, 366

[56] References Cited

U.S. PATENT DOCUMENTS

| | | | |
|---|---|---|---|
| 4,996,435 | 2/1991 | Keller | 250/551 |
| 5,229,871 | 7/1993 | Czarnek et al. | 378/15 |
| 5,336,897 | 8/1994 | Watanabe et al. | 250/551 |

Primary Examiner—Constantine Hannaher
Assistant Examiner—Don Wong
Attorney, Agent, or Firm—Finnegan, Henderson, Farabow, Garrett & Dunner

[57] ABSTRACT

An X-ray CT scanner has a gantry incorporating a stator and a rotator therein. In the gantry, there is provided an optical transmission system for transmitting a light signal concerning the X-ray scan between both the stator and rotator that are opposed to each other in an axial direction of a opening of the gantry in a non-contact state. In the optical transmission system, there are provided a plurality of light emitting elements for emitting the light signal, a light receiving element for receiving the light signal, and a light collector for converging the light signal onto the light receiving element. Each of light emitting elements is equidistantly mounted on a side of the rotator faced to the stator, and the light receiving element is mounted on a side of the stator faced to the rotator, and a light collector is joined with the light receiving element. The light collector is an cone-like member having an aperture for taking in the light signal at one side thereof and a bottom at another side thereof. One side is faced to the another side and the light receiving element is mounted on the bottom. The cone-like member has a mirror-finished inner wall surface and a white-colored inner wall surface.

22 Claims, 8 Drawing Sheets

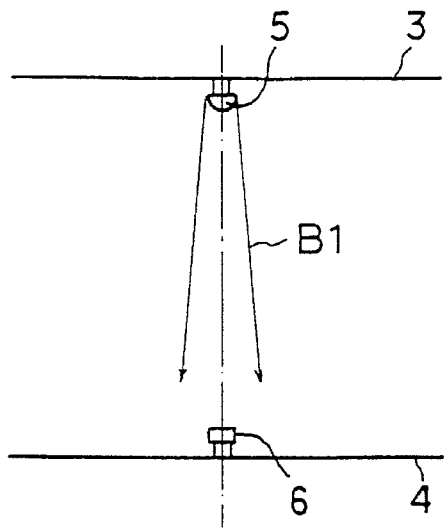
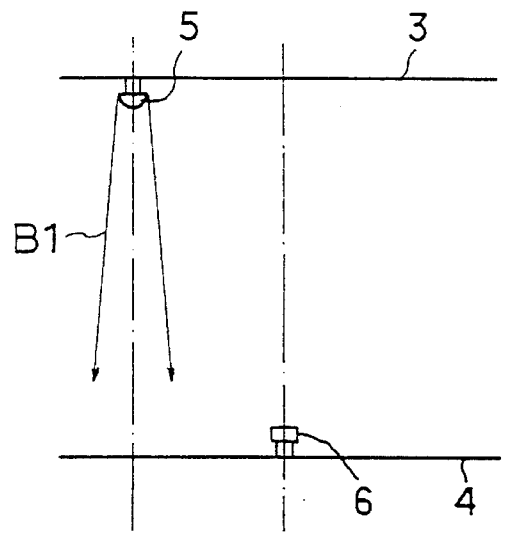
FIG. 5A    FIG. 5B
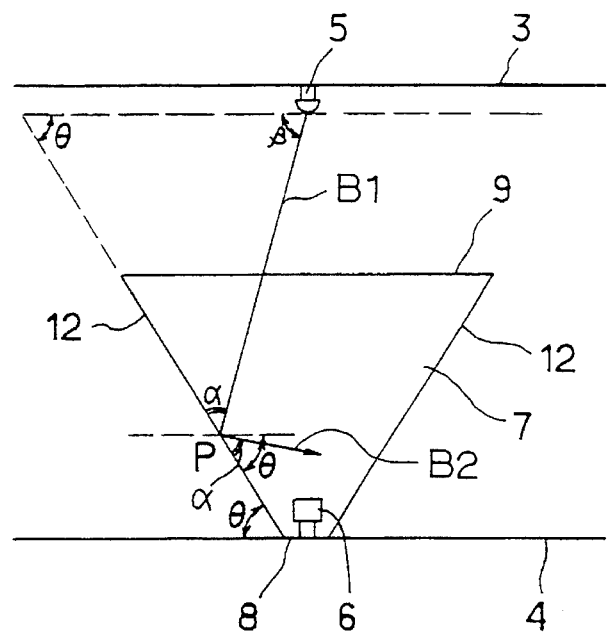
FIG. 6

X-RAY CT SCANNER

BACKGROUND OF THE INVENTION

The present invention relates to an X-ray computed tomography (CT) scanner having an optical transmission system responsible for optical transmission between a rotator and a stator that are arranged to be opposed to each other in a non-contact state in a gantry, both the rotator and stator being arranged therein to perform rotating X-ray beam radiation on a patient inserted into an opening of the gantry.

In recent years, an optical cable has preferably been employed for signal transmission using light signals between a plurality of separated components. When such a plurality of components include moved components, it is very difficult to connect the optical cable to the moved components, thereby the optical cable not being able to be used readily to transmit light signals. Specifically, if the moved components make a rotational motion continuously or repeatedly for a certain period of time, the optical cable would become entangled.

As one of known methods of effecting optical transmission between a moving component and a stationary component that are opposed to each other in a non-contact state, there is an optical system including lenses, reflectors, and others.

For instance, a conventional medical-purpose X-ray CT scanner frequently employs such an optical system. The X-ray CT scanner has a gantry incorporating a stator and a rotator. The rotator, which is formed into a ring shape having an outer circumferential surface, is equipped with an X-ray tube and an X-ray detector at given positions for X-ray diagnosis. On one hand, the stator is made of part of stationary components, for instance, and arranged outside the rotator in its radial direction with an appropriate space left between both of the rotator and stator.

Under such arrangement, the foregoing optical system comprises a plurality of light emitting elements mounted on the outer circumferential surface of the rotator, a light receiving element mounted on the stator, and a plurality of reflectors and lenses arranged in the space between the rotator and stator.

Each of the light emitting elements radially radiates information such as a control signal and an image signal concerning an X-ray scan in the form of a light beam. The radially radiated light beam is to reach the light receiving element with passing complicatedly through the lenses, reflectors, and the like. A light beam has directivity. One light beam, which is propagated by one of the plurality of light emitting elements that has rotated to approach the position opposed at least to the stator, is therefore received readily, but the other light beam propagated by the other light emitting elements located at the other positions is hardly received. The plurality of reflectors, lenses, and the like are therefore arranged between the rotator and stator in order to expand a zone sensitive to incoming light.

In the foregoing prior art that uses the optical system transmitting a light beam in the radial direction, when an attempt is made to improve convergency, it becomes necessary to use high-performance lenses and numerous reflectors in combination. Eventually, the optical transmission system for an X-ray CT scanner becomes very complex and expensive.

SUMMARY OF THE INVENTION

Accordingly, it is an object of the present invention to provide an X-ray CT scanner permitting sensitive optical transmission between a rotator and a stator that are opposed to each other in a non-contact state and arranged in a gantry, and enabling construction of a relatively inexpensive and simple system for the optical transmission.

The above object can be achieved to the present invention, in one aspect by providing an X-ray CT scanner comprising a gantry having an opening for X-ray diagnosis and a rotator and a stator required for X-ray scan, the rotator and stator being opposed to each other in an axial direction of the opening in a non-contact state and at least the rotator being formed into an annular shape, and an optical transmission system for transmitting a light signal concerning the X-ray scan between the rotator and the stator along the axial direction, the optical transmission system comprising a plurality of light emitting elements for emitting the light signal, a light receiving element for receiving the light signal and a light collector for converging the light signal onto the light receiving element, either one of the light emitting elements and the light receiving element being mounted on the rotator, and another one of the light emitting elements and the light receiving element being mounted on the stator.

It is preferred that the light collector is a cone-like member having an aperture at one side of the cone-like member and a bottom at another side of the cone-like member, one side facing the another side and the light receiving element being mounted on the bottom.

It is also preferred that the light emitting elements are mounted on an annular side of the rotator at a constant interval along the annular side and the light receiving element is mounted on a side of the stator, the side of the stator facing the annular side of the rotator.

It is also preferred that the aperture is curved rectangular being equal in curvature to the annular side of the rotator. For instance, the aperture has an area covering at least adjacent two elements of the light emitting elements.

Further, it is preferred that aperture is rectangular. For instance, the aperture has an area covering at least adjacent two elements of the light emitting elements. Further, for instance, the aperture has an area covering adjacent two elements of the light emitting elements at lower end in a radial direction perpendicular to the axial direction.

Further, it is preferred that the cone-like member is made of a resin. For instance, the cone-like member has a mirror-finished inner wall surface. Further, for instance, the cone-like member has a white-colored inner wall surface.

DESCRIPTION OF THE DRAWINGS

The accompanying drawing which are incorporated in and constitute a part of this specification, illustrate embodiments of the present invention and, together with the description, serve to explain the principles of the present invention; in which:

FIG. 5A shows a positional relationship between a light emitting element and a light receiving element which are aligned with the same axis;

FIG. 5B shows a positional relationship between a light emitting element and a light receiving element which are separated from each other;

FIG. 6 is an explanatory diagram illustrating a light beam path in a light collector;

DESCRIPTION OF THE PREFERRED EMBODIMENTS

The first embodiment of the present invention will be described with respect to FIGS. 1 to 6. In this embodiment, the present invention applies to a medical-purpose X-ray CT scanner.

Figure 1:
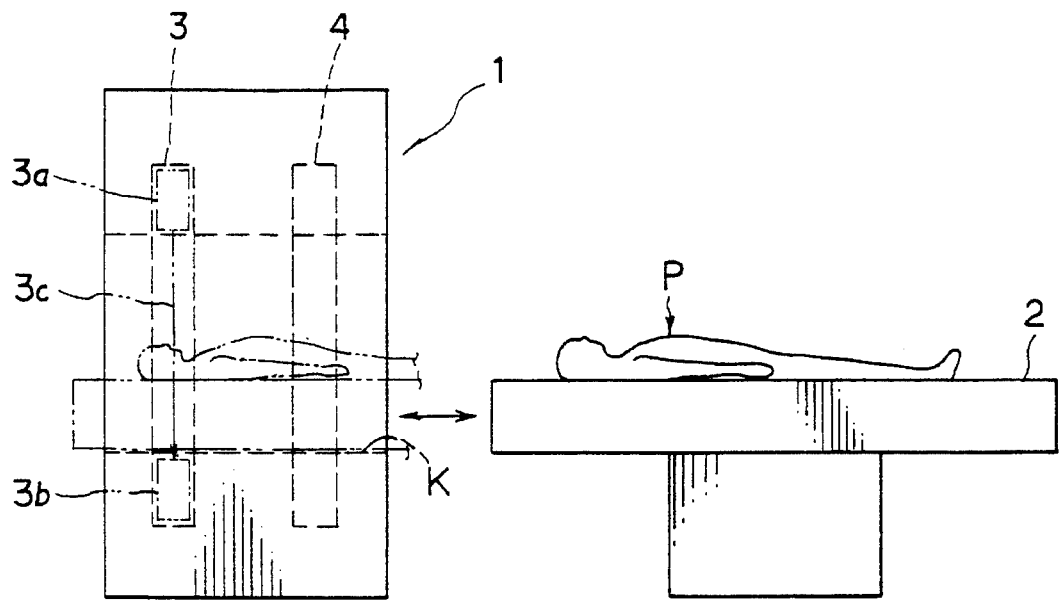
FIG. 1 is a schematic sectional diagram showing an example of components of a medical-purpose X-ray CT scanner in accordance with the present invention.

In a medical-purpose X-ray CT scanner including a gantry 1 and a patient couch 2 which are shown in FIG. 1, the patient couch 2 accommodating a patient P moves in the axial direction of a diagnostic opening K of the gantry 1. The gantry 1 has a rotator 3 and a stator 4, which are formed with annular members and juxtaposed at different positions in the axial direction of the diagnostic opening K.

In the rotator 3, there are provided an X-ray tube 3a for radiating X rays 3c and an X-ray detector 3b for detecting the X rays 3c transmitted through the patient P inserted into the diagnostic opening K. In the diagnostic opening K, the patient P is scanned by radiating X rays 3c from X-ray tube 3a to the X-ray detector 3b while the rotator 3 is rotating. At the same time, both the rotator 3 and stator 4 continuously transmit to each other X-ray image data, a gantry control signal, and others using light signals as media.

As an optical transmission system OS for transmitting each of light signals between both the rotator 3 and stator 4, there are provided a plurality of light emitting elements 5 for emitting light beams B1, a light receiving element 6 for receiving each of light beams B1, and a light collector 7 for converging light beams B1.

Figure 2:
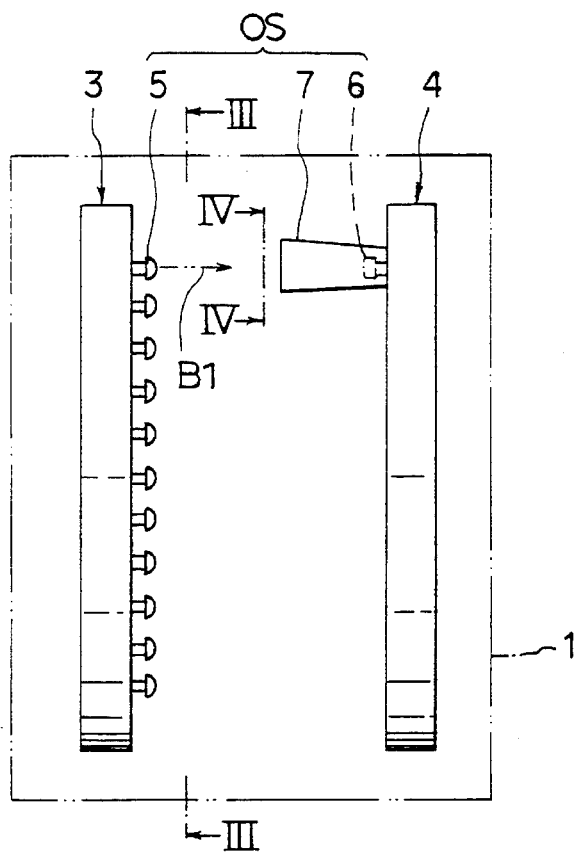
FIG. 2 is a schematic side view showing the inside of gantry of a medical-purpose X-ray CT scanner in the first or second embodiment.
Figure 3:
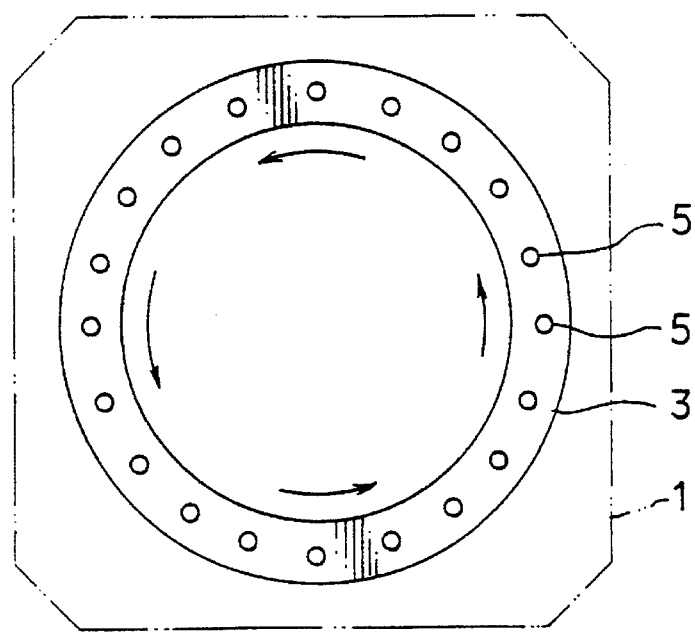
FIG. 3 is a front view of a rotator appearing on the III—III section of FIG. 2.

In FIGS. 2 and 3, the plurality of light emitting elements (for example, light emitting diodes (LEDs)) 5 are mounted on a side of the rotator 3 opposed to the stator 4 at a constant interval. In contrast, in FIG. 2 and FIG. 4, the light receiving element (for example, a photodiode) 6 and the light collector 7 are mounted on a side of the stator 4 opposed to the rotator 3.

Figure 4:
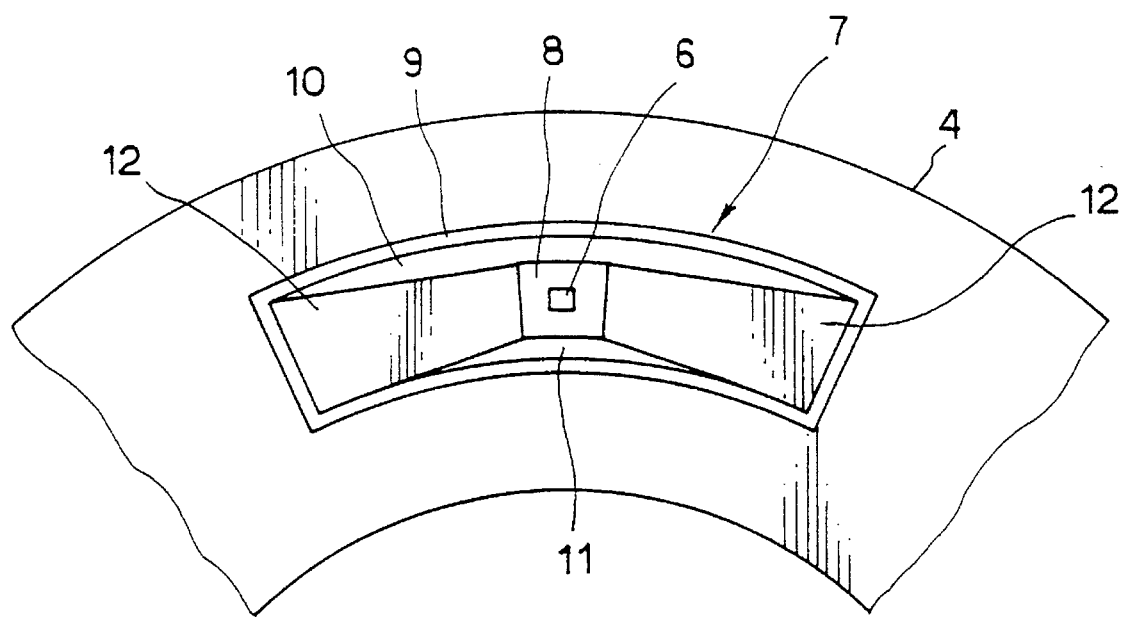
FIG. 4 is a front view of a stator appearing on the IV—IV section of FIG. 2.

The light collector 7 is joined with the stator 4 so as to shield the light receiving element 6. The light collector 7 is a cone-like member which has the tapered inner surface of the present invention that opens on the light emitting elements 5. The cone-like member consists of, as shown in FIG. 4, two apertures; that is, a deep-end aperture 8 and a frontal aperture 9, and four plate members; that is, an outer cover plate 10 whose surface is curved proportionally to the curvature of the annular member, an inner cover plate 11 whose surface is curved proportionally to the curvature of the annular member, and two side plates 12. The deep-end aperture 8 has the light receiving element 6 located in the center thereof. A space fans out from the deep-end aperture 8 toward the frontal aperture 9 while being defined with the four plate members.

The frontal aperture 9 serves as a window for taking in light beams b1 emanating from as many light emitting elements 5 as possible. The frontal aperture 9 is shaped in line with the circular array of light emitting elements 5, or in other words, shaped like a sector curved proportionally to the curvature of the annular member. The outer cover plate 10 and inner cover plate 11, of which surfaces are curved proportionally to the curvature of the annular member, define an isometric trapezoidal space in cooperation with the deep-end aperture 8 and the frontal aperture 9. When viewed from above in FIG. 4, as shown in FIG. 6, the isometric trapezoidal space has the short side defined by the deep-end aperture 8 and the long side defined by the frontal aperture 9. On the other hand, each of the two side plates 12 is, as shown in FIG. 2, shaped like an isometric trapezoid having a bit longer side at the frontal aperture 9 than at the deep-end aperture 8.

An example of dimensions determining an opening state of the light collector 7 in this embodiment will be described.

As shown in FIG. 6, when a light beam B1 emanating from one light emitting element 5 is reflected from a point P on an inner wall of the light collector 7, the angles of incidence and reflection of light at the point P have the same value. Assume that the angle of incidence or reflection shall be indicated as $\alpha$, an angle of intersection formed between the side plate 12 of the light collector 7 and the stator 4 (hereinafter, this angle will be referred to as an aperture angle) shall be indicated, as shown in FIG. 6, as $\theta$, and an angle of intersection formed between a light path dependent on the directivity of the light emitting element 5 and the rotator 3 (hereinafter, this angle will be referred to as a beam angle) shall be indicated as $\beta$. The light beam B1 reflected from the point P (hereinafter, this light beam will be referred to as a first light beam B2) approaches the light receiving element 6 only when the condition below is satisfied:

$$\alpha < \theta \quad (1)$$

This is because unless the condition (1) is satisfied, the first light beam B2 is reflected toward the frontal aperture 9 of the light collector 7 but not converged on the light receiving element 6.

The angle of incidence (reflection) $\alpha$, beam angle $\beta$, and aperture angle $\theta$ are, as shown in FIG. 6, internal angles of a triangle, thus having the following relationship:

$$\alpha + \beta + \theta = \pi \quad (2)$$

wherein $\pi$ represents 180° ($\pi$ radian).

The light collector 7 is therefore designed to have the aperture angle θ satisfying the above conditions (1) and (2) so as to reflect at least the first light beam B2 toward the light receiving element 6.

The function of the this embodiment will be described with respect to FIGS. 5 and 6.

First, the plurality of light emitting elements 5 continuously transmit light beams B2 toward the stator 4 while the rotator 3 is rotating.

Now, light reception will be discussed on the assumption that, as shown in FIGS. 5A and 5B, the light collector 7 is not employed.

A light beam has directivity. Therefore, for example, when one of the plurality of light emitting elements 5 is substantially aligned with the light receiving element 6 as shown in FIG. 5A, the light beam B1 sent from the light emitting element 5 is converged substantially on the vicinity of the distal end of the light receiving element 6. Thus, light reception is enabled. However, as shown in FIG. 5B, when the light emitting element 5 is separating from the light receiving element 6 with the rotation of the rotator 3, the light beam B1 sent from the light emitting element 5 is hardly converged on the vicinity of the distal end of the light receiving element 6. Thus, light reception is almost disabled. The above positional relationship is concerned with one light emitting element 5. The same applies to each of the plurality of light emitting elements 5 mounted on the rotating rotator 3.

Next, light reception will be discussed on the assumption that the light collector 7 is joined with the light receiving element 6.

When one of the light emitting elements 5 and the light receiving element 6 has the positional relationship shown in FIG. 5A, as mentioned above, light reception is enabled without the light collector 7. In this state, the light beam B1 emanating from the light emitting element 5 spreads at a certain angle toward the light receiving element 6 so as to propagate in a direction determined by a beam angle β dependent on the directivity of the light emitting element 5.

The portion of the spreading the light beam B1 around the center thereof advances substantially straight, passes through the frontal aperture 9 of the light collector 7, and then enters around the distal end of the light receiving element 6.

On the other hand, at least the portion of the spreading light signal away from the center thereof passes through the frontal aperture 9 of the light collector 7, collides against the inner wall of the light collector 7 at an angle α, and then reflects from the inner wall at the same angle α. At this time, the light collector 7 has an aperture angle θ satisfying the conditions (1) and (2). Since the aperture angle θ has a larger value than the angle of incidence (reflection) α, the first light beam B2 converges on the light receiving element 6.

In contrast, when one of the light emitting elements 5 and the light receiving element 6 has the positional relationship shown in FIG. 5, the light beam B1 sent from the light emitting element 5 having rotated to become substantially opposed at least to the frontal aperture 9 of the light collector 7 passes through the frontal aperture 9, and then collides against the inner wall of the light collector 7. The first light beam B2 then converges on the light receiving element 6 similarly to the portion of the spreading light beam B1 away from the center thereof shown in FIG. 5A.

As mentioned above, when the positional relationship shown in FIG. 5A is attained, the light collector 7 contributes to further improvement of light reception sensitivity. When the positional relationship shown in FIG. 5B is attained, the light collector 7 helps expand the light reception Merely by combining the light collector 7 with the one light receiving element 6, light beams sent from the plurality of light emitting elements 5 can be converged efficiently. Compared with prior art, this embodiment has the advantage of converging light at relatively low cost without a high-performance lens or a plurality of reflectors.

Next, the second embodiment of the present invention will be described with respect to FIGS. 7 to 14.

A medical-purpose X-ray CT scanner in accordance with this embodiment is tantamount to a materialization of an actual design concept. A difference from the first embodiment lies in that a light collector is shaped differently. The hardware of the X-ray CT scanner is identical to that in the first embodiment. The identical components bear the same reference numerals.

Figure 7:
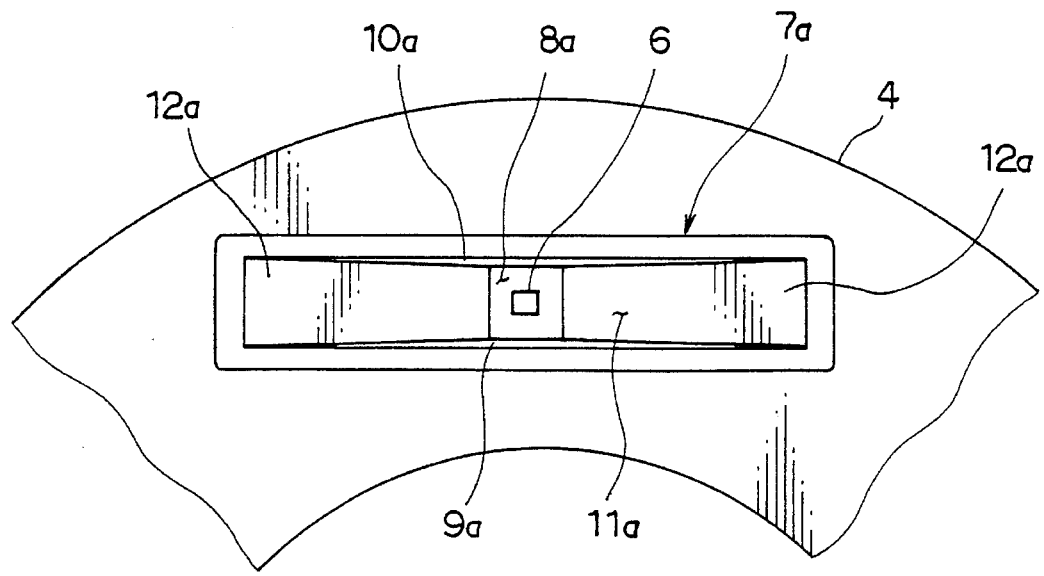
FIG. 7 is a front view of a rotator, which appears on the III—III section of FIG. 2, in an X-ray CT scanner in accordance with the second embodiment.
Figure 8:
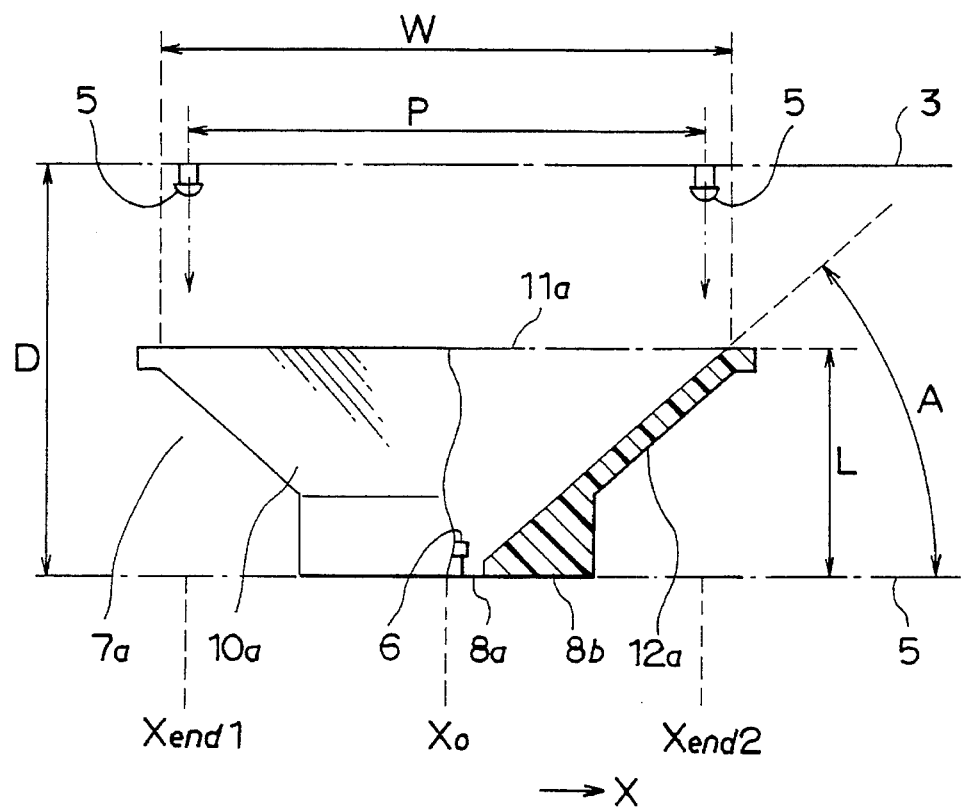
FIG. 8 is an explanatory diagram illustrating an example of dimensions defining a shape of a light collector in the second embodiment.

A light collector 7a as shown in FIGS. 7 and 8 has a deep-end aperture 8a and a frontal aperture 9a each of which is shaped like a rectangle. Due to the rectangular shape, four plate members; that is, an outer cover plate 10a, an inner cover plate 11a, and two side plates 12a are flat. In addition, a mount 8b is formed around the deep-end aperture 8a in order to enable mounting of the light collector 7a to the stator 5.

An example of dimensions of the light collector 7a; that is, set values of the aperture angle A, aperture width W, and length L from the deep-end aperture 8a to the frontal aperture 9a under the conditions for keeping at constant values of the distance D between a rotator 3 and a stator 4, and interval P between adjoining light emitting elements 5 will be described on with respect to FIGS. 8 to 11.

Figure 9:
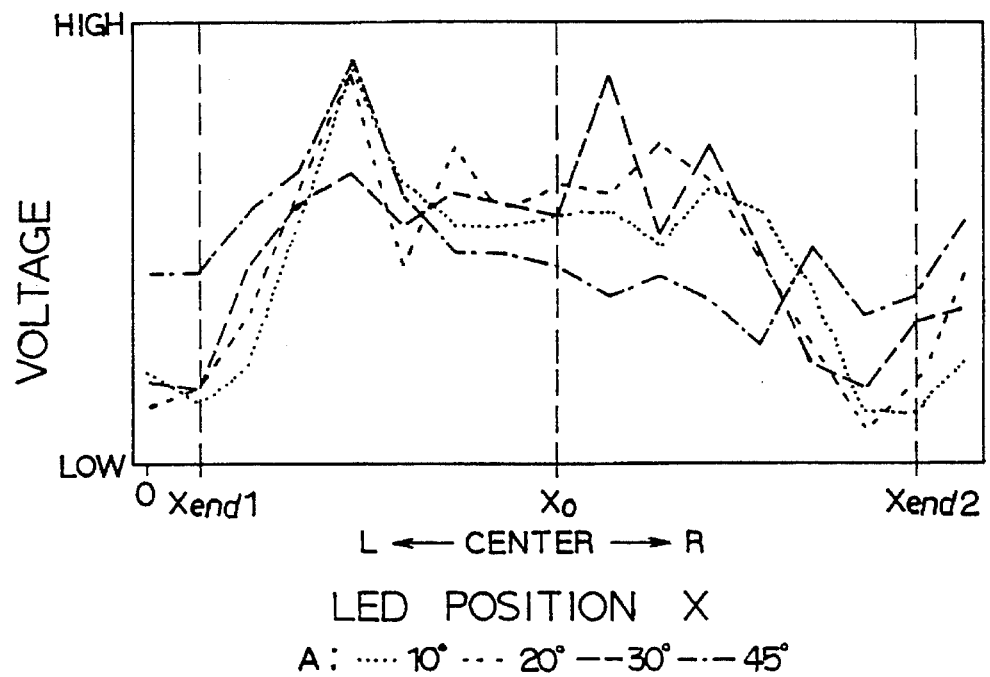
FIG. 9 is a graph plotting results of an simulation conducted under the condition that an aperture angle of a light collector ranges from 0° to 45°.
Figure 10:
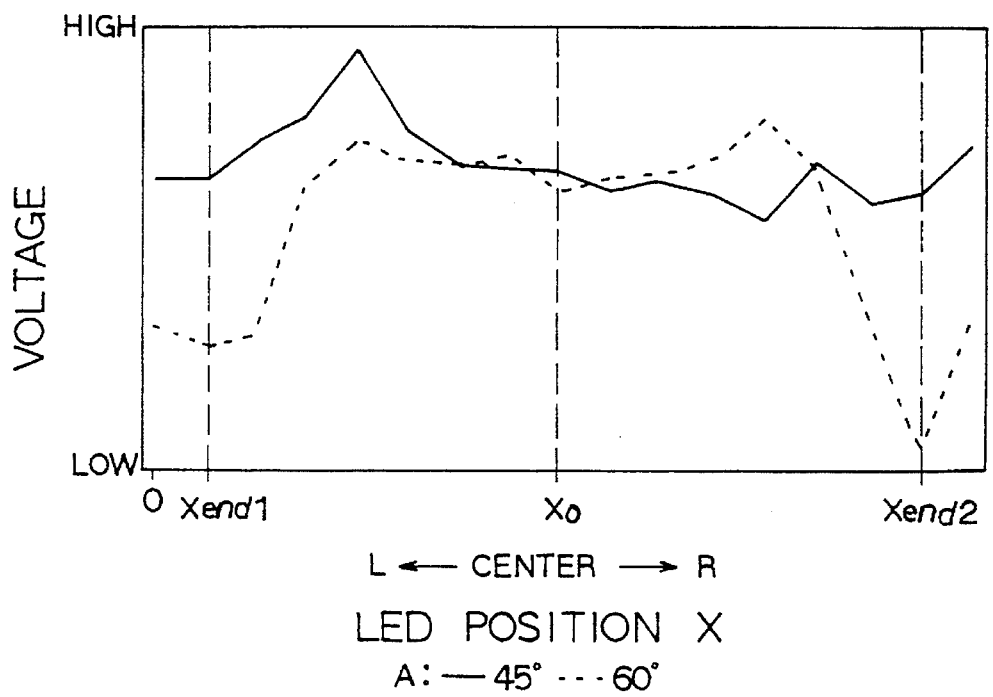
FIG. 10 is a graph plotting results of an simulation conducted under the condition that an aperture angle of a light collector ranges from 45° to 60°.

First, based on the results of simulations as shown in FIGS. 9 and 10, the aperture angle A of the light collector 7a is set to the range from about 40° to 45°. The simulations whose results are plotted as FIGS. 9 and 10 are intended to study the light receiving capability of the light collector 7a by changing in value the aperture angle A (for example, A=10° to 60°) under the conditions for keeping at a constant value of the aperture width W shown in FIG. 8. Specifically, while one of the light emitting elements (LEDs) is rotating to shift from one edge of the frontal aperture 9a to the other edge thereof via a position at a center $X_o$ shown in FIGS. 8 to 10, values of voltage resulting from photoelectric transformation performed by the light receiving element are measured.

In terms of the resultant average values of the voltage measured at positions near both edges of the frontal aperture 9a; that is, at positions at which the light receiving capability of the light receiving element is thought to deteriorate most (for example, positions at Xend 1 and Xend 2 shown in FIGS. 8 to 10), it has been concluded that the preferred aperture angle A of the light collector 7a is about 45°.

Figure 11:
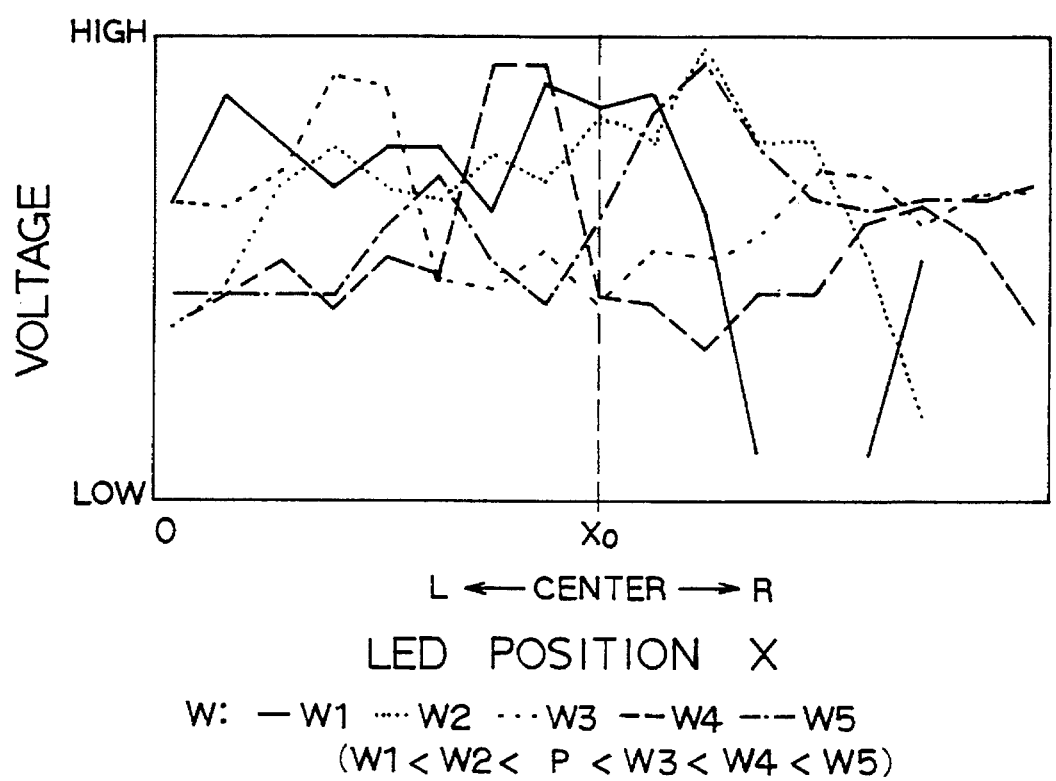
FIG. 11 is a graph plotting results of an simulation conducted under the condition for changing in the value of an aperture width of a light collector.

Next, based on the results of a simulation as shown in FIG. 11, the aperture width W of the light collector 7a is set to the value for covering at least adjacent two elements of the light emitting elements. The simulation whose results are plotted as FIG. 11 is intended to study, similarly to the aforesaid simulation, the voltage values corresponding to the light receiving capability of the light collector 7a by changing in value the aperture width W of the light collector 7a from W1 to W5 (W1<W2<P<W3<W4<W5) under the conditions for keeping at a constant value of the aperture angle A (for example, A=45°) shown in FIG. 8.

Consequently, the simulation has revealed that when the aperture width W has a smaller value than the interval P between adjoining light emitting elements (for example, W=W1 and W2 shown in FIG. 11), the voltage plunges down abruptly in the course of light reception and therefore transmission of a light signal is almost disabled. In this embodiment, therefore, for the purpose of continuous transmission of a light signal, the aperture width W is set to a value larger than the interval P; that is, to a value permitting simultaneous acceptance of at least two light emitting elements.

Incidentally, because there is almost no difference in the light receiving capability when the aperture widths are W3 to W5 ( larger than the interval P as shown in FIG. 11), it is preferred that the aperture width W is set to the smallest value (for instance, W=W3). This selection of size of W enables the most possible compact form of the light collector 7a, which means that the mounting space at the rotator side for electrical parts required to emit light beams is ensured.

Next, the material of the light collector 7a and the state of the inner wall thereof will be described.

Based on the workability of a material, a resin offering excellent workability has been selected as a material to be made into the four plate members of the light collector 7a. The inner walls of the light collector are colored white that optically offers an excellent reflection characteristic.

Figure 12:
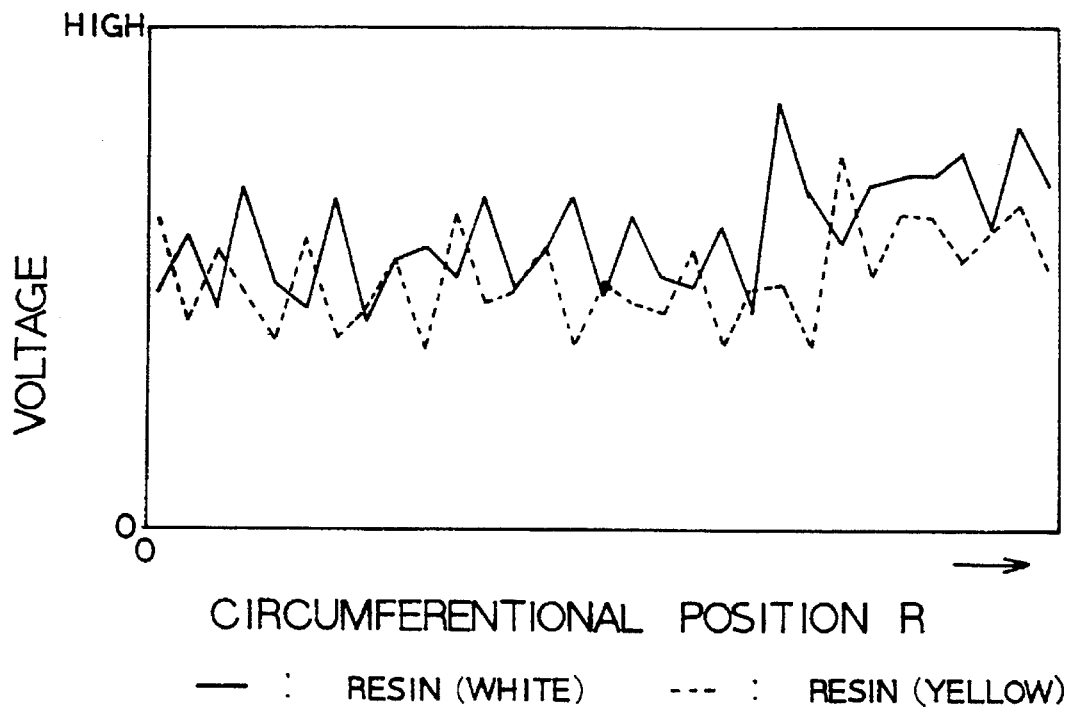
FIG. 12 is a graph plotting results of an simulation under the condition that light collectors having inner walls colored differently are studies in comparison.
Figure 13:
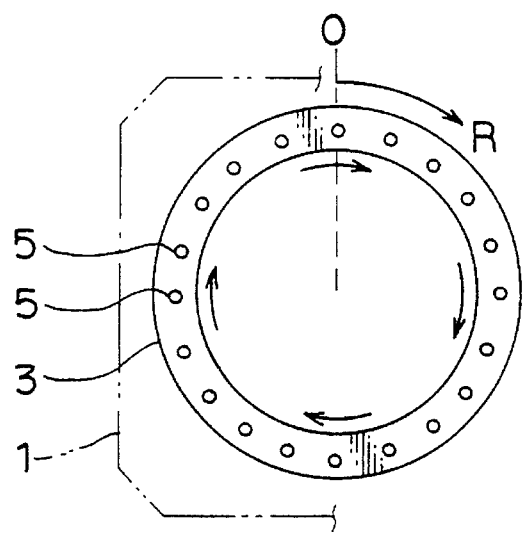
FIG. 13 is an explanatory diagram illustrating the conditions for the simulations whose results are plotted as FIG. 12.

The light collector being made of an resin was used to conduct an simulation whose results are plotted as FIG. 12. This simulation was conducted under the conditions for changing in a value of circumferential position R during rotation of the rotator 3 shown in FIG. 13, wherein assuming that an inner wall of a light collector had been discolored (for example, changed from white to yellow) as a result of a secular change, the light receiving capability of the light collector was studied. The simulation has revealed that a light collector being made of an resin and having the inner wall colored in yellow provides lower voltage values on the average than a light collector having the inner wall colored in white while the rotator 3 is rotating. Even in the light collector having had the inner wall colored in yellow and provided the lower voltage values, the average values cause no significant problem in practice.

Figure 14:
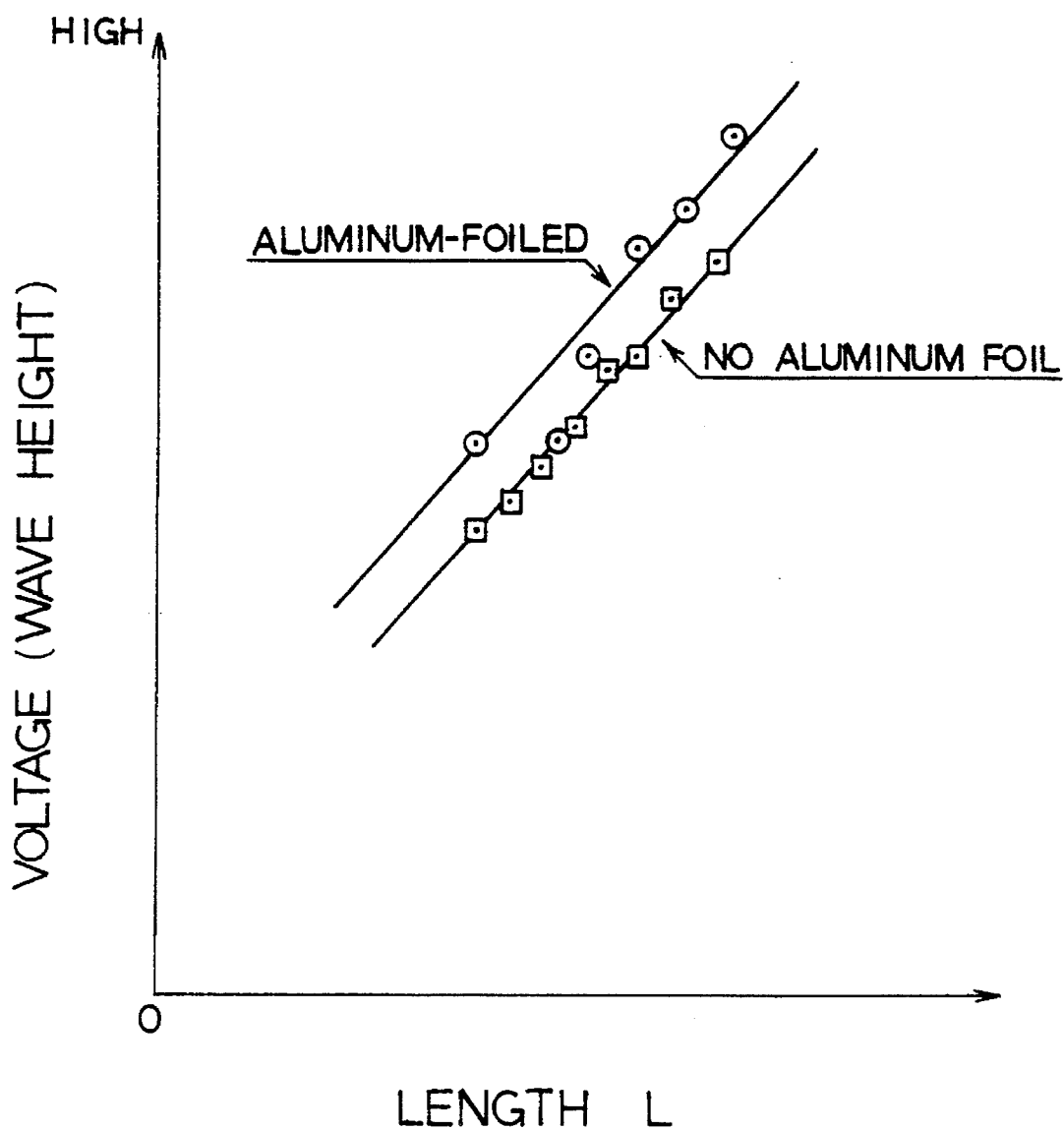
FIG. 14 is a graph plotting results of an simulation under the condition that light collectors having inner walls finished differently are studied in comparison.

Next, based on the results of an simulation shown in FIG. 14, an inner wall of a light collector has been polished to be a mirror-finished surface. The simulation whose results are plotted as FIG. 14 was conducted in an effort to improve the light receiving capability of the light collector 7a by changing in a value of the length L under the conditions for keeping at constant values of the aperture angle A and the aperture width W shown in FIG. 8, wherein the state of the inner wall of the light collector 7a was studied. Particularly, a light collector having a thin aluminum foil attached to the inner wall; that is, having a mirror-finished surface as the inner wall was compared with a light collector having the inner wall left intact in terms of the light receiving capability.

Consequently, the simulation has revealed that the voltage corresponding to a wave height is proportional to the length L of a light collector, and that the light collector having an aluminum foil provides higher voltage values on the average than the normal light collector irrelevant of the length L of the light collector.

As mentioned above, since the light collector 7a is designed to have the aforesaid dimensional values, light beams sent from at least two light emitting elements 5 is caught by the frontal aperture 9a of the light collector 7a, and reflected toward the light receiving element 6 by the white and mirror-finished inner wall of the light collector 7a. In the medical-purpose X-ray CT scanner of the second embodiment, while the rotator 3 is rotating, light beams emanating from the light emitting elements 5 can be supplied to the light receiving element 6 efficiently and unintermittently.

In the medical-purpose X-ray CT scanner of the first or second embodiment, light emitting elements are mounted on a rotator and a light receiving element is mounted on a stator. The present invention is not necessarily limited to this structure. Alternatively, the reverse will do. That is to say, the light receiving element may be mounted on the rotator and the light emitting elements may be mounted on the stator.

When both the light emitting elements and light receiving element are mounted on each of the rotator and stator, bi-directional optical transmission can be achieved between the rotator and stator.

The present invention is not limited to an optical transmission system in a gantry of a medical-purpose X-ray CT scanner. The present invention may apply to an optical transmission system responsible for data transmission between a moving component and a stationary component which are opposed to each other in a non-contact state.

For instance, when the optical transmission system is to be installed in the patient couch 2 in FIG. 1, the frontal aperture 9 of the light collector 7 is re-shaped in line with the array of light emitting elements. The aperture width is determined in consideration of an interval between adjoining light emitting elements and whether or not signal transmission should be continuous. Thus, optical transmission can be achieved satisfactorily between a member moving along the axis of the patient couch 2 and a stator.

Aside from the medical-purpose X-ray CT scanner, the present invention can apply to a belt conveyer or the like at a factory that is controlled through optical transmission. In this case, the shape of the light collector 7 and the aperture width thereof must be changed. The shape of the frontal aperture of the light collector is not limited to a sector and a rectangle which are adopted in the embodiments.

What is claimed is:

1. An X-ray CT scanner comprising:

a gantry having X-ray diagnostic opening therethrough, and a rotator and a stator required for an X-ray scan, the rotator and stator being opposed to each other in an axial direction of the opening in a non-contact state and at least the rotator being formed into an annular shape; and an optical transmission system for transmitting a light signal concerning the X-ray scan between the rotator and the stator along the axial direction, the optical transmission system comprising a plurality of light emitting elements for emitting the light signal, a light receiving element for receiving the light signal and a light collector for converging the light signal onto the light receiving element, one of the light emitting elements and the light receiving element being mounted on the rotator, and another of the light emitting elements and the light receiving element being mounted on the stator, wherein the light collector is a cone-like member having an aperture at one side and a bottom at another side, the one side facing the other side, and the light receiving element being mounted at the bottom of the light collector.

2. An X-ray CT scanner according to claim 1, wherein said light emitting elements are mounted on an annular side of the rotator at a constant interval along the annular side and said light receiving element is mounted on a side of the stator, said side of the stator facing the annular side of the rotator.

3. An X-ray CT scanner according to claim 1, wherein said aperture is curved rectangular being equal in curvature to the annular side of the rotator.

4. An X-ray CT scanner according to claim 3, wherein said aperture has an area covering at least two adjacent light emitting elements.

5. An X-ray CT scanner according to claim 4, wherein the light collector is made of a resin.

6. An X-ray CT scanner according to claim 5, wherein the cone-like member has a mirror-finished inner wall surface.

7. An X-ray CT scanner according to claim 5, wherein the cone-like member has a white-colored inner wall surface.

8. An X-ray CT scanner according to claim 1, wherein said aperture is rectangular.

9. An X-ray CT scanner according to claim 8, wherein said aperture has an area covering two adjacent light emitting elements at lower end in a radial direction perpendicular to the axial direction.

10. An X-ray CT scanner according to claim 9, wherein the light collector is made of a resin.

11. An X-ray CT scanner according to claim 10, wherein the cone-like member has a mirror-finished inner wall surface.

12. An X-ray CT scanner according to claim 10, wherein the cone-like member has a white-colored inner wall surface.

13. An X-ray CT scanner according to claim 8, wherein the aperture has an area covering at least two adjacent light emitting elements.

14. An X-ray CT scanner according to claim 1, wherein said aperture has an area covering at least two adjacent light emitting elements.

15. An X-ray CT scanner according to claim 1, wherein said cone-like member is made of a resin.

16. An X-ray CT scanner according to claim 15, wherein said cone-like member has a mirror-finished inner wall surface.

17. An X-ray CT scanner according to claim 15, wherein said cone-like member has a white-colored inner wall surface.

18. An X-ray CT scanner according to claim 1, wherein each of the plurality of light emitting elements is a light emitting diode.

19. An X-ray CT scanner according to claim 1, wherein said light receiving element is a photodiode.

20. An X-ray CT scanner according to claim 1, wherein the cone-like member has a mirror-finished inner wall surface.

21. An X-ray CT scanner according to claim 1, wherein the cone-like member has a white-colored inner wall surface.

22. An X-ray CT scanner according to claim 1, wherein the cone-like member has a tapered inner surface.

* * * * *